US008119031B2

(12) United States Patent
Lloyd et al.

(10) Patent No.: US 8,119,031 B2
(45) Date of Patent: *Feb. 21, 2012

(54) MIXED SOLUBILITY BORATE PRESERVATIVE

(75) Inventors: Jeffrey D. Lloyd, Knoxville, TN (US); Mark J. Manning, Santa Monica, CA (US); Frederick M. Ascherl, Parker, CO (US)

(73) Assignee: U.S. Borax Inc., Greenwood Village, CO (US)

( * ) Notice: Subject to any disclaimer, the term of this patent is extended or adjusted under 35 U.S.C. 154(b) by 649 days.

This patent is subject to a terminal disclaimer.

(21) Appl. No.: 12/288,673

(22) Filed: Oct. 22, 2008

(65) Prior Publication Data

US 2009/0053509 A1    Feb. 26, 2009

Related U.S. Application Data

(63) Continuation of application No. 10/332,549, filed as application No. PCT/US01/22391 on Jul. 16, 2001, now Pat. No. 7,449,130.

(60) Provisional application No. 60/218,954, filed on Jul. 17, 2000.

(51) Int. Cl.
    *C09K 3/00* (2006.01)
(52) U.S. Cl. ........ 252/385; 264/109; 428/526; 428/527; 428/528; 524/14
(58) Field of Classification Search .................. 252/385; 264/109; 428/526, 527, 528; 524/14
    See application file for complete search history.

(56) References Cited

U.S. PATENT DOCUMENTS

| 629,861 | A | 8/1899 | Konrad |
| 4,076,580 | A | 2/1978 | Panusch et al. |
| 4,126,473 | A | 11/1978 | Sobolev et al. |
| 4,352,719 | A | 10/1982 | Herr |
| 4,363,798 | A | 12/1982 | Seavey |
| 4,661,157 | A | 4/1987 | Beauford et al. |
| 4,879,083 | A | 11/1989 | Knudson et al. |
| 4,935,457 | A | 6/1990 | Metzner et al. |
| 5,047,275 | A | 9/1991 | Chiu |
| 5,207,823 | A | 5/1993 | Shiozawa |
| 5,246,652 | A | 9/1993 | Hsu et al. |
| 5,478,598 | A | * 12/1995 | Shiozawa ............... 427/297 |
| 5,516,472 | A | 5/1996 | Laver |
| 5,549,739 | A | 8/1996 | Inoue et al. |
| 5,612,094 | A | 3/1997 | Schubert et al. |
| 5,763,338 | A | 6/1998 | Sean |
| 5,972,266 | A | 10/1999 | Fookes et al. |
| 6,030,562 | A | 2/2000 | Lehtinen et al. |
| 6,153,293 | A | 11/2000 | Dahl et al. |
| 6,368,529 | B1 | 4/2002 | Lloyd et al. |
| 6,582,732 | B1 | 6/2003 | Bender et al. |
| 2001/0037035 | A1 | 11/2001 | Kutcel |
| 2003/0071389 | A1 | 4/2003 | Manning et al. |

FOREIGN PATENT DOCUMENTS

| CA | 836519 | 3/1970 |
| DE | 3537241 A1 | 4/1987 |
| DE | 3805819 A1 | 9/1988 |
| JP | 62-275703 A | 11/1987 |
| JP | 63-137802 A | 6/1988 |
| JP | 63-159006 A | 7/1988 |
| JP | 63-135599 A | 9/1988 |
| JP | 63-237902 A | 10/1988 |
| JP | 04-219201 | 8/1992 |
| JP | 06-155412 A | 6/1994 |
| JP | 11-514364 | 12/1999 |
| WO | WO-00/09326 | 2/2000 |
| WO | WO-02/13605 A2 | 2/2002 |

OTHER PUBLICATIONS

Wytner, abstract of Patent No. PL 158853 B, Oct. 30, 1992.
T. Sean, G. Burnette and F. Cote, "Protection of Oriented Strandboard with Borate", Forest Product Journal, vol. 49, No. 6, Jun. 1999, pp. 47-51.
P.E. Laks and M.J. Manning, "Inorganic Borates as Preservative Systems for Wood Composites", Second Pacific Rim Bio-Based Composites Symposium, Vancouver, Canada, Nov. 6-9, 1994, pp. 236-244.
P.E. Laks and M.J. Manning, "Preservation of Wood Composites with Zinc Borate", International Research Group on Wood Preservation 26th Annual Meeting, Helsinger, Denmark, Jun. 11-16, 1995, pp. 1-12.
P.E. Laks and M.J. Manning, "Update on the Use of Borates as Preservatives for Wood Composites", Proceedings of the Second International Conference on Wood Protection with Diffusible Preservatives and Pesticides, pp. 62-68, Forest Products Society, Madison, Wisconsin 1997.
Taubert et al., Chemical Abstracts, 85, 34930 (1976).
Taubert et al., Chemical Abstracts, 85, 169499 (1977).
Chemische Fabrik Kalk GmBh., Chemical Abstracts, 89, 94230 (1977).
Sprague et al., Chemical Abstracts, 92, 43489 (1979).
Kataflox Patentvervaltungs G.M.B.H., Chemical Abstracts, 92,115446, (1979).
Kataflox Patentvervaltungs G.M.B.H., Chemical Abstracts, 92, 133957 (1979).
Sobolov et al., Chemical Abstracts, 94, 49097 (1980).

(Continued)

Primary Examiner — Cephia D Toomer
(74) Attorney, Agent, or Firm — Kurt R. Ganderup

(57) ABSTRACT

Preservative composition for lignocellulosic-based composites providing rapid and long-lasting protection against insect and fungal attack, in both low and high moisture environments, through the use of a combination of higher solubility and lower solubility borates. Pesticidal amounts of a lower solubility borate and a higher solubility borate are combined before or during their incorporation into a lignocellulosic-based composite. Useful low solubility borates include copper borate, zinc borate and barium metaborate. Useful high solubility borates include boric acid, boric oxide, ammonium borate and alkali metal borates such as sodium borate. Some alkaline earth metal borates, including calcium borates, calcium magnesium borates, magnesium borates and calcium sodium borates, are of intermediate solubility and may be used effectively as either a low soluble or high soluble borate depending on the combination used.

13 Claims, No Drawings

OTHER PUBLICATIONS

Herr, A.K., Chemical Abstracts, 117374 (1981).
Herr, A.K., Chemical Abstracts, 95, 152447 (1981).
Taubert, R., Chemical Abstracts, 95, 221614 (1981).
Taubert, R., Chemical Abstracts, 97, 94323 (1982).
Taubert, R., Chemical Abstracts, 99, 40094 (1983).
Herr, A.K., Chemical Abstracts, 102, 206153 (1985).
Oestman, B.A.L., et al., Chemical Abstracts, 103, 38898, (1984).
Herr, A.K., Chemical Abstracts, 106, 104112 (1986).
Sugiura et al., Chemical Abstracts, 108, 136813 (1988).
Nekota, T., Chemical Abstracts, 129, 71147 (1998).
Jansen, W., Derwent World Patent Index Abstract, DE 3206218 A (1983).
Herr, A.K., Chemical Abstracts, 107, 117264 (1987), Re: Patent No. DE 3537241 A1 (English language abstract of citation #11).
John Simonsen, Jeffrey J. Morrell and Camille Freitag, "Effect of Woodfiber/Plastic Ratio and Biocide Addition on Durability of Woodfiber-Plastic Composites", 6th International Conference on Woodfiber-Plastic Composites, Madison, Wisconson, May 15-16, 2001, pp. 9-10 (Abstract).
John Simonsen, Camille Freitag and Jeffrey J. Morrell, "Effect of Wood-Plastic Ratio on the Performance of Borate Biocides Against Brown Rot Fungi", proceedings of 6th International Conference on Woodfiber-Plastic Composites, Madison, Wisconsin; pp. 69-72, complimentary proceedings mailed to authors and notices sent to conference attendees regarding availability of proceedings on Feb. 19, 2002.
Sunyoung Lee and Qinglin Wu, "Leachability of Zinc Borate-Modified Oriented Strandboard (OSB) from Southern Wood Species", Forest Products Society 55th Annual Meeting, Baltimore, Maryland, Jun. 24-27, Poster Presentation Abstract—p. 31, Booth 6.
Will A. Jones, Terry L. Amburgey, H. Michael Barnes, Terry Sellers Jr. and George E. Woodson, "Leachability of Zinc Borate-Modified Oriented Strandboard (OSB) from Southern Wood Species", Forest Products Society 55th Annual Meeting, Baltimore, Maryland, Jun. 24-27, Poster Presentation Abstract—p. 32, Booth 8.
Thomas H. Daniels and Douglas P. Krapas, "Combustion Characteristics of Zinc Borate-Impregnated OSB Wood Waste in an Atmospheric Fluidized Bed", 32nd International Particleboard/Composite Materials Symposium Proceedings, Washington State University, Pullman, Washington, Mar. 31-Apr. 2, 1998, p. 167 (Abstract).
Thomas H. Daniels and Douglas P. Krapas, "Combustion Characteristics of Zinc Borate-Impregnated OSB Wood Waste in a Fluidized Bed Combustion System", 32nd International Particleboard/Composite Materials Symposium Proceedings, Mar. 31-Apr. 2, 1998, Energy Products of Idaho, pp. 1-11.
R. B. Donovan, "Choice of refractories of treated wood waste burners", NZ Timber Journal, May 2, 1966, pp. 42-43.
W. Young, "The Effect of Lime on Clinker Formed in Furnaces Burning Boric Acid Impregnated Planer Shavings", Australian Timber Journal, vol. 12, No. 12, pp. 690, 693, 700, 701 (1947).
Sprague et al., "The use of boron products in cellulose insulation", Journal of Thermal Insulation, vol. 2, Apr. 1979, pp. 161-174.
Peter E. Laks and Steven A. Verhey, "Decay and Termite Resistance of Thermoplastic/Wood Fiber Composites", 5th Pacific Rim Bio-Based Composites Symnposium, Canberra, Australia Dec. 2000.
Steven Verhey, Peter Laks and Dana Richter, "Laboratory Decay Resistance of Woodfiber/Thermoplastic Composites", Forest Products Journal, vol. 51, No. 9, pp. 44-49, Sep. 2001.
Inorganic Chemistry Inst., Derwent World Patent Index Abstract, SU 283546, WPI Acc. No. 71-45842S/27 (1971).
Matsushita Elec. Works, Derwent World Patent Index Abstract, JP 63179810, WPI Acc. No. 88-246688/35 (1988).
Meisei et al., Derwent World Patent Index Abstract, JP 60155565, A (1983).
Ota et al., Chemical Abstracts, 109, 192457 (1988).
Nakai et al., Chemical Abstracts, 109, 20676 (1988).
International Search Report for Application No. PCT/US01/22391, 2001.
International Preliminary Examination Report for Application No. PCT/US01/22391, 2001.
Official Action issued by the Canadian Patent Office on Apr. 23, 2009, for Canadian Application No. 2,416,297.
Official Action issued by the Canadian Patent Office on Mar. 17, 2010, for Canadian Application No. 2,416,297.
English summary of Official Action issued by the Chilean Patent Office, received on Nov. 15, 2004, for Chilean Application No. 1698-2001.
English summary of Official Action issued by the Chilean Patent Office, received on Jun. 15, 2006, for Chilean Application No. 1698-2001.
English summary of Official Action issued by the Chilean Patent Office, received on Jun. 15, 2007, for Chilean Application No. 1698-2001.
English translation of Official Action issued by the Japanese Patent Office on Jul. 5, 2011, for Japanese Application No. 2002-512313.
Substantive Examination: Examiner's Report issued by the Malaysian Patent Office on Aug. 1, 2006, for Malaysian Application No. PI 20013371.
Substantive Examination: Clear Report issued by the Malaysian Patent Office on Jul. 29, 2008, for Malaysian Application No. PI 20013371.
Official Action (with English summary) issued by the Venezuelan Patent Office on Apr. 17, 2007, for Venezuelan Application No. 2001-001516.

* cited by examiner

MIXED SOLUBILITY BORATE PRESERVATIVE

This application is a continuation of U.S. application Ser. No. 10/332,549, which was the National Stage of International Application No. PCT/US01/22391, filed Jul. 16, 2001, now U.S. Pat. No. 7,449,130, the entire contents of which are incorporated herein by reference, which claims the benefit under 35 U.S.C. 119(e) of U.S. Provisional Application No. 60/218,954, filed Jul. 17, 2000.

FIELD OF THE INVENTION

This invention relates to the preservation of lignocellulosic-based composites and more particularly to the protection of composite products against insect and fungal attack through the use of mixed solubility borate preservative combinations.

BACKGROUND OF THE INVENTION

Due to recent changes in the species, size and quality of standing timber available for harvest throughout the world, composites of lignocellulosic materials have replaced traditional solid sawn lumber for use in many structural applications. Many of these composites are used in applications, which require resistance to wood-destroying organisms such as fungi and various insects. Accordingly, this requires treatment with a wood preservative.

Traditionally, solid wood products are dipped or pressure treated with solutions of preservative chemicals. However, the nature of a composite material makes it possible to incorporate a preservative into the product during its manufacture. This decreases total production costs and yields a superior product in which the composite has a constant loading of preservative throughout its thickness.

Borates have been used as broad-spectrum wood preservatives for over 50 years. Their benefits include efficacy against most wood destroying organisms such as fungi, termites and wood-boring beetles. Coupled with their low acute mammalian toxicity and low environmental impact, their fungicidal and insecticidal properties have resulted in them being considered the wood preservative of choice for most structural or construction applications. Borates such as boric acid, borax, disodium octaborate tetrahydrate (commercially available as Tim-bor® Industrial Wood Preservative from U.S. Borax Inc.) and, more recently, zinc borate are well accepted as wood preservatives. Generally, boric acid, borax and disodium octaborate are used for treating solid wood products by dip or pressure treatment. However, these preservatives are readily soluble in water and can be incompatible with many resin systems used in producing composite products, resulting in an adverse effect on the internal bond strength of the resultant composites and poor mechanical strength. Anhydrous borax and zinc borate have been used successfully at relatively low levels with some resin systems, such as the phenol-formaldehyde resins, to produce composites with acceptable internal bond strength. See Knudson et al., U.S. Pat. No. 4,879,083. Zinc borate is also particularly preferred because its inherent low solubility reduces leaching and loss of the active ingredients in laboratory tests and in high moisture hazard environments in service. Although the low solubility borates of Knudson et al., especially zinc borate, have been used successfully to treat wood composites such as oriented strand board (OSB), waferboard, fiberboard and particleboard, they suffer from several specific problems related to their low solubility. For example, while they perform very well in laboratory decay tests in high humidity situations, or after leaching, if the tests are carried out without leaching and at lower ambient relative humidities (20-30% moisture content in the wood) a limited amount of fungal decay can occur.

This invention provides composites made from wood and other lignocellulosic materials which are resistant to attack by wood destroying organisms such as fungi and insects, have excellent internal bonding strength, low inherent leaching and yet still provide both rapid and long-lasting performance against decay fungi and insects at low as well as high moisture content.

SUMMARY OF THE INVENTION

According to this invention, a pesticidal amount of a lower solubility borate and a higher solubility borate, in combination, are incorporated into lignocellulosic-based composites, thereby producing composites which have rapid, yet long-lasting, resistance against insect and fungal attack in low moisture and high moisture environments.

DETAILED DESCRIPTION OF THE INVENTION

The mixed solubility borate formulations of this invention can be prepared by well known blending or mixing of the two or more variably soluble borates. Generally, a larger proportion of the lower solubility borate component is used in combination with a smaller proportion of the higher solubility borate component. Weight ratios of the lower solubility component to the higher solubility component as low as 0.1:1 or as high as 9:1 can give improvement over using a single borate, but the preferred ratio is in the range of between about 1:1 and 3:1 for low soluble component to high soluble component.

Blending of the two or more components if carried out prior to addition to the lignocellulosic matrix or resin binder may be done using batch or continuous methods. Any suitable means of blending may be used, such as a V-blender, rotary blender, zig zag blender, pin blender, paddle or ribbon blender, fluidized bed blender, conical screw blender, or air flow blender. In addition to using a simple blend, the mixed borate formulation can be prepared by coating the low soluble borate component with the high soluble borate component or by intimately combining them both with a binder (e.g. water) such as by using a pan granulator. Such coated or granulated combinations are beneficial in preventing segregation of the two components during transport etc. and prior to incorporation into the composite. They also improve product distribution and reduce segregation within the composite.

The low solubility and high solubility borates which are combined to be used in the method of this invention may be any one or more of the high soluble borate compounds such as boric acid and boric oxide, ammonium borate or alkali metal borates such as the sodium borates borax pentahydrate, borax decahydrate, sodium pentaborate, disodium octaborate, and sodium metaborate; and any one or more of the low solubility borate compounds such as transition metal borates (e.g. copper borates, zinc borates), or barium metaborate. Some alkaline earth metal borates, including calcium borates, calcium magnesium borates, magnesium borates and calcium sodium borates are of intermediate solubility and can be used effectively as either a low soluble or high soluble borate depending on the combination used. For example, a formulation comprising an intermediate solubility borate, such as calcium borate, and a high solubility borate, such as sodium borate, would provide an effective mixed solubility borate formulation according to this invention, and such would be the preferred for use in a low moisture environment such as in interior sheathing. Similarly, a formulation comprising an intermediate solubility borate, such as calcium borate, and a low solubility borate, such as zinc borate, would provide an effective mixed solubility borate formulation, and such would be preferred for use in a high moisture hazard environment such as in exterior siding.

The preferred sodium borates are the sodium tetraborates, the sodium octaborates and the sodium pentaborates. Such sodium borates may be synthetically produced or may be a naturally occurring borate, such as tincal, tincalconite or kemite.

The preferred zinc borates are the zinc polytriborates, having a $ZnO:B_2O_3$ ratio of 2:3. A number of polytriborates are known and these metal oxide formulations can be described using the metal oxide to boron oxide to water ratios. Suitable polytriborates as examples include the 2:3:3.5 (sometimes referred to as 4:6:7), the 2:3:7 and the 2:3:7.5, or with the full formulae $2ZnO.3B_2O_3.3.5H_2O$, $2ZnO.3B_2O_3.7H_2O$, and $2ZnO.3B_2O_3.7.5H_2O$, respectively. Other suitable hydrated zinc borates include the 3:5:14, the 1:1:2 (where the 2 is probably actually 1.67) and the 4:1:1 or with the full formulae $3ZnO.5B_2O_3.14H_2O$ (also referred to incorrectly as $2ZnO.3B_2O_3.9H_2O$), $ZnO.5B_2O_3.14H_2O$, where x is about 1.67 (this compound is typically referred to as either $ZnO.B_2O_3.2H_2O$ or $2ZnO.2B_2O_3.3H_2O$) and $4ZnO.B_2O_3.H_2O$, respectively. Such zinc borates are synthetically produced.

Suitable copper borates include a number of known compounds, but also amorphous mixtures of borate and copper. Examples include $[Cu(NH_3)_4]O.2B_2O_3.6H_2O$ (cuprammine borate hexahydrate). This compound is typically the first crop of crystals one obtains upon concentrating ammoniacal "copper borate" solutions, i.e., borax and copper sulfate dissolved in ammonia solution. It is metastable and decomposes to other copper and cuprammine borates upon standing in solution. Known or reported suitable copper borate compounds include the mixed metal oxide $3Na_2O.2CuO.8B_2O_3.17H_2O$ as well as the 4:1:5, 3:2:3, 2:1:1 and 1:1:2 copper borates or, with the full formulae, $4CuO.B_2O_3.5H_2O$, $3CuO.2B_2O_3.3H_2O$, $2CuO.B_2O_3.H_2O$, and $CuO.B_2O_3.2H_2O$, respectively. Such suitable copper borates are synthetically produced.

The preferred calcium borates are the calcium polytriborates, having a $CaO:B_2O_3$ ratio of 2:3, and calcium hexaborates, having a $CaO:B_2O_3$ ratio of 1:3, with the most preferred being the calcium polytriborates. Such calcium polytriborates may be synthetically produced or may be a naturally occurring borate, such as inyonite, meyerhofferite and colemanite. Examples of suitable calcium hexaborates include nobleite and gowerite. Calcium-sodium borates and calcium-magnesium borates include probertite, ulexite and hydroboracite.

The particle size of the combined borates is not critical, but should be of a size that can be readily dispersed throughout the composite product. Generally, a mean particle size of as large as about 500 microns and as small as about 1 micron may be used, but for best results, it is preferred that the particle size be in the range of from about 150 microns to about 10 microns. It is also generally advantages for the two borates being mixed to have similar particle sizes to aid in the blending operation.

The effective amount of mixed borate formulation incorporated in the composite is a pesticidal amount; that is, an amount sufficient to control or kill fungi (e.g. mold and decay fungi) and/or insects that destroy wood and similar cellulosic-based composite products. Generally, a range of from about 0.1 to about 4 percent by weight of the formulation, based on the composite product is used to control pests. The amount used will depend on the target pests, desired performance longevity and the expected level of precipitation exposure. Preferably, from about 0.5 to about 2 percent is used for optimum performance against both decay fungi and termites. Loadings as low as 0.05 percent by weight can have a favorable effect against some mold organisms.

The mixed borate formulations are considered to have a low impact on the environment, with low mammalian toxicity, resulting in relatively safe use and disposal. They are effective fungicidal and insecticidal compounds that are relatively inexpensive, easy to store, handle and use. Further, the borate formulations have some immediate water solubility, providing rapid and continuing pesticidal activity in composites subject to exposure to low moisture environments in uses such as interior sheathing, but also a reservoir of more slowly released active ingredients to provide very long term performance and performance under high moisture hazard environments such as exterior siding.

The lignocellulosic-based composites of this invention are produced by well known procedures by combining particles of the lignocellulosic material with an adhesive binder and forming the composite, generally with heat and pressure. The mixed solubility borate formulations of this invention may be pre-mixed and incorporated by adding to the lignocellulosic particles and/or binder, prior to forming the composite. Alternatively, the higher solubility borate and lower solubility borate may be introduced separately from one another, for example sequentially or simultaneously, e.g. from separate hoppers and feeders, during manufacture of the composite, to form a mixed preservative in situ. In cases where a composite is manufactured in multiple layers, the borate preservative of this invention may be implemented by incorporating a high solubility borate in one or more layers and a low solubility borate into a different layer or layers. Preferably, a more soluble borate is incorporated into an inner layer or layers and a less soluble borate is incorporated into one or more outer layers. Incorporation of the two different borates into different layers of a multi-layer composite may also provide a particular advantage in cases where one type of resin or lignocellulose particle is used in a core or inner layer and a different resin or particle system is used in the outer layers since, for example, some resin systems may be adversely effected by the use of a high solubility borate, while others may not be effected.

Lignocellulosic-based composites are formed from small fractions of cellulosic material, which are bonded with an adhesive binder, generally with heat and under pressure. The method of forming cellulosic-based composites is well known and has resulted in many products, including particleboard, oriented strand board (OSB), waferboard, fiberboard (including medium-density and high-density fiberboard), parallel strand lumber (PSL), laminated strand lumber (LSL), laminated veneer lumber (LVL), and similar products. Examples of suitable cellulosic materials include wood, straw (including rice, wheat and barley), flax, hemp and bagasse. The small fractions of cellulosic material can be in any processed form such as chips, flakes, fibers, strands, wafers, trim, shavings, sawdust, straw, stalks and shives.

The methods for manufacturing composites are well known and the specific procedure will be dependent on the cellulosic raw material and the type of composite desired. However, generally the cellulosic material is processed into fractions or particles of appropriate size, which may be called a furnish, mixed with an adhesive binder and the resultant mixture is formed into the desired configuration such as a mat, and then formed, usually under pressure and with heat, into the final product. The process could be considered an essentially dry process; that is, generally, no water is added to form a slurry of the materials (other than any water that may be used as a carrier for liquid resins).

The binder is preferably an adhesive resin that is cured with heat to give a strong bond between the cellulosic particles or fractions and provide structural composites with high mechanical strength. Such heat-cured adhesive resins are well known and include the formaldehyde- and isocyanate-based resins. Phenol-formaldehyde, phenol-resorcinol-formaldehyde, urea-formaldehyde, melamine-urea-formaldehyde and diphenylmethanediisocyanate (pMDI) are examples of suitable heat-cured resins in current use. The preferred levels of binder can typically range from about 1.5% to about 15% by weight of the finished wood composite, but may be as low as 0.5% or as high as 25% for some composites, depending on a variety of constraints such as the particle size of the furnish and the strength and durability required of the finished wood composite. For example, structural quality OSB would typically contain between about 1.5% and 7% binder, whereas structural quality particle board may require up to 15 to 20% binder or more and medium density fiberboard (MDF) with low strength and durability requirements, such as pegboard, may contain less than 1%. Unlike many borates that have been used in the past to preserve cellulosic-based composites, the mixed borate formulation of the present invention may be used successfully, without adverse effect on the binder or on the mechanical strength of the composite product. Another application for the mixed solubility preservatives of this invention is in the emerging area of woodfiber-plastic composites where wood is mixed with thermoplastic binders such as high density polyethylene, polypropylene or polyvinyl chloride. In this application the mixed solubility preservative compositions may be incorporated into woodfiber-plastic composites containing thermoplastic binder levels up to about 30-50% by weight of the finished wood composite.

The mixed borate formulation may be incorporated in the composite in any manner that will result in dispersion throughout the final product. In the case of wood-based composites, it may be mixed with the wood particles, or furnish, prior to mixing with the resin or it may be added to the resin or wood-resin mixture and then formed into a mat for pressing, heating and curing to produce the final composite. Preferably, the mixed borate formulation is evenly distributed on wood particles such as chips or strands, in order to maximize contact between the wood particles and the preservative, then the resin is applied and the wood furnish is spread evenly onto plates or an endless belt (conveyor belt), forming a mat to be pressed into its final thickness. Heat is applied to cure the resin and form the final composite product. The wood furnish may contain optional amounts of additives, such as slack wax or flow agents, if desired, to aid in processing or performance, but are not essential.

EXAMPLES

The following examples illustrate the novel preservative compositions and methods of this invention.

Example 1

Wood composite samples were made having a phenol-formaldehyde (PF) resin face and a diphenylmethanediisocyanate (pMDI) resin core. Some of the samples included a combination of the zinc borate, $2ZnO.3B_2O_3.3.5H_2O$, (ZB) and disodium octaborate tetrahydrate (DOT) and others contained ZB alone, while still others contained no wood preservative. The ZB/DOT combination formulations contained 60% ZB by weight and 40% DOT. The preservative compositions were added to the wood composite samples at a loading of 0.1% by weight of the wood composite. The samples were cut to 50 mm×25 mm×20 mm before testing. A total of eight samples from each treatment set were subjected to decay testing.

A total of eight samples from each treatment set were tested according to a standard European decay test protocol known as EN113. The samples were first sealed in plastic bags and gamma irradiated at a level of at a level of 2.0 Mrad using a $^{60}Co$ source to ensure sterilization prior to mono-culture decay testing.

Aqueous solutions of 2.0% malt and 2.0% agar were prepared and then autoclaved at 120° C. for 30 minutes. The solutions were allowed to cool to between 50° C. and 80° C. and were then poured into pre-autoclaved animal jars (dimensions: height=7 cm, diameter=9 cm) with approximately 100 ml per jar. The jars were placed into a container, kept in a temperature-controlled room at 22° C. (±2° C.) and observed for two days. After the jars were ensured to be free of contamination, they were inoculated with a mature culture of *Coniophora puteana* (brown rot—Basidimycotina). Inoculated jars were incubated at 22° C. (±2° C.) until the mycelium covered between ⅔ and 9/10 of the solid agar substrate.

All specimens were placed on sterilized plastic mesh to prevent agar contact and water logging. The gamma-irradiated wood composites were then placed onto the fungal cultures. The jar lids were loosely screwed on to allow for air exchange. Following introduction of the samples to the cultures, the animal jars were again incubated at 22° C. (±2° C.) for a period of twelve weeks. The composites were then oven dried at 80° C. overnight and then weighed to determine the percent weight loss resulting from the fungal decay.

The decay results are shown in Table 1, expressed as average percent weight loss of the wood composite samples after 12 weeks of fungal decay exposure. These results show that the mixed solubility product is better at inhibiting fungal decay than the zinc borate alone.

TABLE 1

| Wood Composites | Average % Wt. Loss | % error |
| --- | --- | --- |
| control | 23.05 | 0.53 |
| ZB only | 15.98 | 0.81 |
| ZB(60)/DOT(40) | 12.02 | 0.74 |

Example 2

The effectiveness of the mixed solubility wood preservatives of this invention against mold growth was tested on samples of aspen oriented strand board (OSB). Two OSB formulations were evaluated. One type was bonded with pMDI resin at a 6% loading. The other type was bonded with a PF resin face and a pMDI resin core. The OSB samples contained either a mixed solubility borate preservative formulation or a low solubility borate alone, or no preservative in the case of the control samples. The low solubility borate in all cases was zinc borate 2:3:3.5. The two different high solubility borates were tested—disodium octaborate tetrahydrate (DOT) and boric oxide ($B_2O_3$), also known as anhydrous boric acid (ABA). The weight ratio of low solubility borate to high solubility borate in the mixed solubility samples was either 80/20 or 60/40. Two different target loadings of preservative in the OSB samples were tested—0.18% and 0.88% by weight.

Mold exposure testing was carried out using a modified version of the ASTM: D 3273-94 procedure. Exposure of the OSB samples to mold was done in an experimental chamber consisting of a 597 mm×311 mm×413 mm plastic container tilted on its side to give a 45° roof angle to prevent condensate dripping on the samples and filled with 2-3 inches of water. The water was heated to 32.5° C. (±1° C.), using a thermostatically controlled heating coil. A 292 mm×394 mm×133 mm plastic bowl was filled to within 3 inches from the top with a mixture of damp potting soil and unsterile soil collected from outdoors to provide an inoculum source for mold. The bowl was floated in the plastic container. The boards were placed on a plastic mesh above the inoculum source. The blocks were inverted at one week intervals. The test ran for a duration of 4 weeks.

After the four week mold exposure, the samples were examined visually and rated for mold formation on a scale of 0 to 4, with 0 representing no mold formation (i.e. complete control) and 4 representing complete coverage or overgrowth of the sample by mold. The results are presented in Table 2. The borate loading (i.e. 0.18% v. 0.88%) had a significant effect, with the higher loading providing better control, as expected. With regard to the ratio of high solubility borate to low solubility borate, the samples containing 40% soluble borate (i.e. 60% zinc borate) provided a significant improvement over the samples containing 0% soluble borate (i.e. 100% zinc borate), on average. Furthermore, significantly greater mold growth was observed at the faces of the OSB board samples compared to the edges.

TABLE 2

| Target Borate Loading % BAE | Soluble Borate | Board | Mold Formation Measured at | Rating at x % High Solubility Borate | | |
|---|---|---|---|---|---|---|
| | | | | x = 0 | x = 20 | x = 40 |
| 0.18 | ABA | pMDI-6% | Edges | 2.00 | 2.00 | 2.00 |
| 0.18 | ABA | PF-pMDI | Edges | 2.00 | 1.50 | 1.75 |
| 0.18 | DOT | pMDI-6% | Edges | 2.00 | 1.75 | 2.00 |
| 0.18 | DOT | PF-pMDI | Edges | 2.00 | 2.25 | 1.75 |
| Average | | | | 2.00 | 1.88 | 1.88 |
| 0.88 | ABA | pMDI-6% | Edges | 0.75 | 1.50 | 0.25 |
| 0.88 | ABA | PF-pMDI | Edges | 1.50 | 2.00 | 0.75 |
| 0.88 | DOT | pMDI-6% | Edges | 0.75 | 0.75 | 1.25 |
| 0.88 | DOT | PF-pMDI | Edges | 1.50 | 1.25 | 1.50 |
| Average | | | | 1.13 | 1.38 | 0.94 |
| 0.18 | ABA | pMDI-6% | Faces | 0.75 | 1.00 | 0.50 |
| 0.18 | ABA | PF-pMDI | Faces | 1.25 | 0.88 | 0.25 |
| 0.18 | DOT | pMDI-6% | Faces | 0.75 | 0.75 | 1.25 |
| 0.18 | DOT | PF-pMDI | Faces | 1.25 | 1.88 | 0.38 |
| Average | | | | 1.00 | 1.13 | 0.59 |
| 0.88 | ABA | pMDI-6% | Faces | 0.00 | 0.63 | 0.00 |
| 0.88 | ABA | PF-pMDI | Faces | 0.75 | 0.75 | 0.25 |
| 0.88 | DOT | pMDI-6% | Faces | 0.00 | 0.63 | 0.00 |
| 0.88 | DOT | PF-pMDI | Faces | 0.75 | 0.75 | 0.25 |
| Average | | | | 0.38 | 0.69 | 0.13 |

Example 3

Another set of mold tests similar to Example 2 was carried out. Test samples consisted of Aspen OSB bonded with pMDI resin at a 6% loading. The OSB samples were treated with a hydrophobic resin 1% EW-58S, manufactured by Borden, which served as a water repellant. The preservative treated OSB samples contained either zinc borate alone or a mixture of zinc borate and DOT, at a 60/40 weight ratio. Target loadings of preservative were 0.05, 0.10 and 0.20% by weight in the OSB samples. The OSB test samples were cut into 76 mm×102 mm panels for use in the mold testing. Mold exposure testing was carried out using essentially the same method described in Example 2, except that the water was heated to 30.5° C. (±1° C.). The relative humidity within the environmental chamber was monitored and maintained at 95 to 99% with an average temperature of 27 to 30° C.

After the four week mold exposure, the samples were examined visually and rated for mold growth on a scale of 0 to 4, as in Example 2. The results are presented in Table 3. These results show consistently better control of mold growth for the samples containing a mixture of 40% by weight DOT (60% zinc borate) compared with samples containing 100% by weight zinc borate and no high solubility borate.

TABLE 3

| Target Borate Loading % BAE | Mold Formation Measured at | Rating at x % DOT | |
|---|---|---|---|
| | | x = 0 | x = 40 |
| 0.05 | Faces | 1.00 | 0.33 |
| 0.05 | Edges | 1.00 | 0.67 |
| 0.10 | Faces | 2.67 | 0.67 |
| 0.10 | Edges | 3.33 | 0.67 |
| 0.20 | Faces | 1.00 | 1.00 |
| 0.20 | Edges | 2.33 | 1.67 |
| Average | | 1.89 | 0.84 |

Example 4

The performance of mixed solubility borate preservatives against termites was investigated in a study using aspen waferboards bonded with either 100% pMDI (in both face and core) or with Phenol Formaldehyde (PF) in the face and pMDI in the core. The boards were made with a target loading of 0.88% preservative utilizing the formulations (blends) described in Table 4. The borates were incorporated into the board by mixing the preservative formulations with the aspen wafers in a blender before addition of the adhesive and wax. Composite board specimens were exposed to the Formosan subterranean termite (*Coptotermes formosanus* Shiraki) at a field test site in Hilo, Hi. The specimens, along with untreated aspen 'feeder' stakes, are placed in a horizontal array on hollow core concrete blocks approximately 10 cm thick. In addition to surrounding the test specimens, the untreated feeder stakes are also driven into the ground in an effort to increase the termite pressure on the test specimens. The assembly is then covered with a wooden box to prevent direct contact with rain. This is a severe test format conducted using a very termite susceptible wood species (aspen).

After 3, 9 and 15 months exposure the boards were rated visually on a scale of 0 to 10. A rating of 10 indicates the sample was in perfect condition, while a 0 rating means the sample was essentially destroyed. Each result consisted of an average rating from the inspection of 10 separate samples (10 replicates).

The results are summarized in Table 4. In the boards made with the PF/pMDI resin system, the 80/20 and 60/40 mixed solubility preservative blends outperformed low solubility preservative alone (100% ZB) after 9 and 15 months exposure in this rigorous, accelerated termite test.

TABLE 4

| Board | Borate Preservative Composition (wt. %) | | | Termites Ratings | | |
|---|---|---|---|---|---|---|
| | ZB | DOT | ABA | 3 mos. | 9 mos. | 15 mos. |
| pMDI | 100 | 0 | 0 | 10 | 9.8 | 9.9 |
| pMDI | 80 | 20 | 0 | 10 | 9.9 | 9.9 |
| pMDI | 60 | 40 | 0 | 10 | 9.9 | 9.9 |
| pMDI | 80 | 0 | 20 | 10 | 9.8 | 9.9 |
| pMDI | 60 | 0 | 40 | 10 | 9.6 | 10 |
| PF/pMDI | 100 | 0 | 0 | 10 | 9.5 | 9.7 |
| PF/pMDI | 80 | 20 | 0 | 10 | 9.9 | 9.9 |
| PF/pMDI | 60 | 40 | 0 | 10 | 9.8 | 10 |
| PF/pMDI | 80 | 0 | 20 | 10 | 9.7 | 10 |
| PF/pMDI | 60 | 0 | 40 | 10 | 9.9 | 9.9 |

Various changes and modifications of the invention can be made and, to the extent that such variations incorporate the spirit of this invention, they are intended to be included within the scope of the appended claims.

What is claimed is:

1. A preservative composition for lignocellulosic-based composites comprising a higher solubility borate and a lower solubility borate, wherein said higher solubility borate is selected from the group consisting of boric acid, boric oxide, ammonium borate, borax pentahydrate, borax decahydrate, sodium pentaborate, disodium octaborate, sodium metaborate, calcium borate, calcium magnesium borate, magnesium borate and calcium sodium borate, and the lower solubility borate is selected from the group consisting of copper borate, zinc borate and barium metaborate, and wherein the higher solubility and lower solubility borates combined have a mean particle size of between about 500 microns and about 1 micron.

2. A preservative composition according to claim 1 wherein the higher solubility borate is selected from the group consisting of boric acid, boric oxide, and ammonium borate.

3. A preservative composition according to claim 1 wherein the higher solubility borate is selected from the group consisting of borax pentahydrate, borax decahydrate, sodium pentaborate, disodium octaborate, and sodium metaborate.

4. A preservative composition according to claim 1 wherein the higher solubility borate is selected from the group consisting of calcium borate, magnesium borate, calcium magnesium borate and calcium sodium borate.

5. A preservative composition according to claim 1 wherein the lower solubility borate is zinc borate.

6. A preservative composition according to claim 1 wherein the weight ratio of the lower solubility borate to the higher solubility borate is in the range of from about 0.1:1 to about 9:1.

7. A preservative composition according to claim 1 wherein the weight ratio of the lower solubility borate to the higher solubility borate is in the range of from about 1:1 to about 3:1.

8. A lignocellulosic-based composite having resistance against insect and fungal attack which contains lignocellulosic-based furnish, resin binder and a pesticidal amount of a preservative composition comprising a higher solubility borate and a lower solubility borate, wherein the higher solubility borate is selected from the group consisting of boric acid, boric oxide, ammonium borate, borax pentahydrate, borax decahydrate, sodium pentaborate, disodium octaborate, sodium metaborate, calcium borate, calcium magnesium borate, magnesium borate and calcium sodium borate, and the lower solubility borate is a low solubility borate selected from the group consisting of copper borate, zinc borate and barium metaborate, and wherein the higher solubility and lower solubility borates combined have a mean particle size of between about 500 microns and about 1 micron.

9. A lignocellulosic-based composite according to claim 8 wherein the weight percent of the preservative composition is at least about 0.1% of the composite.

10. A lignocellulosic-based composite according to claim 8 wherein the weight percent of the preservative composition is in the range of from about 0.5% to about 2% of the composite.

11. A lignocellulosic-based composite according to claim 10 wherein the weight percent of the preservative composition is up to about 1% of the composite.

12. A method for protecting a lignocellulosic-based composite against insect and fungal attack comprising incorporating into the composite a pesticidal amount of a preservative composition comprising a higher solubility borate and a lower solubility borate, wherein said higher solubility borate is selected from the group consisting of boric acid, boric oxide, ammonium borate, borax pentahydrate, borax decahydrate, sodium pentaborate, disodium octaborate, sodium metaborate, calcium borate, calcium magnesium borate, magnesium borate and calcium sodium borate, and the lower solubility borate is a low solubility borate selected from the group consisting of copper borate, zinc borate and barium metaborate, and wherein the higher solubility and lower solubility borates combined have a mean particle size of between about 500 microns and about 1 micron.

13. A composite board comprising lignocellulosic-based furnish, a thermoplastic binder and a preservative amount of the composition according to claim 1.

* * * * *